United States Patent [19]

Hutchings et al.

[11] Patent Number: 5,076,960

[45] Date of Patent: Dec. 31, 1991

[54] DEODORIZING AND CLEANING COMPOSITIONS AND METHOD

[75] Inventors: Richard S. Hutchings, Fairfield; Mary K. Haber, Cincinnati, both of Ohio

[73] Assignee: The Drackett Company, Cincinnati, Ohio

[21] Appl. No.: 425,738

[22] Filed: Oct. 23, 1989

[51] Int. Cl.$^5$ .............................................. C01B 11/10
[52] U.S. Cl. ........................... 252/186.33; 252/186.36; 252/187.23
[58] Field of Search ...................... 252/186.36, 186.37, 252/187.1, 187.23, 186.33

[56] References Cited

U.S. PATENT DOCUMENTS

| | | | |
|---|---|---|---|
| 3,156,654 | 11/1964 | Konecny | 252/186.33 |
| 3,580,850 | 5/1971 | Dupre | 252/187.23 |
| 3,580,851 | 5/1971 | Heid | 252/187.23 |
| 3,629,124 | 12/1971 | King | 252/187.23 |
| 4,036,776 | 7/1977 | Riegel et al. | 252/187.23 |
| 4,156,662 | 5/1979 | Wilson et al. | 252/174.11 |
| 4,198,309 | 4/1980 | Mookherjee et al. | 252/174.11 |
| 4,332,691 | 6/1982 | Beavan | 252/187.23 |
| 4,711,741 | 12/1987 | Fujishima et al. | 252/187.23 |
| 4,783,193 | 11/1988 | Pensa | 252/186.36 |

*Primary Examiner*—Robert L. Stoll
*Assistant Examiner*—Joseph D. Anthony
*Attorney, Agent, or Firm*—Wyatt, Gerber, Burke & Badie

[57] ABSTRACT

Aqueous deodorizing and cleaning compositions having a pH of from about 4 to 11 containing defined quantities of an alkali metal halogenite together with a salt of a transition or post-transition metal.

13 Claims, No Drawings

DEODORIZING AND CLEANING COMPOSITIONS AND METHOD

FIELD OF THE INVENTION

The present invention refers to aqueous compositions containing an alkali metal halogenite, for example sodium chlorite ($NaClO_2$) together with a salt of a transition or post transition metal or mixtures thereof in a sufficient quantity to increase the efficacy of the alkali metal halogenite solution for cleaning and/or odor elimination. It relates also to such compositions containing one or more selected ligands and stabilizing alcohols.

BACKGROUND OF THE INVENTION

Aqueous compositions of alkali metal halogenites, especially sodium chlorite, are known. Such compositions appear to function in either of two ways.

In one mode of action, the metal chlorite itself acts as an oxidant. For example, when used as an odor eliminator, the chlorite oxidizes the amines, aldehydes and thiols which are the principal components of malodorous mixtures and converts them to odorless oxidation products. In the second mode of action, the halogen dioxide, principally chlorine dioxide, performs the same function.

Halogenites such as sodium chlorite when they are a sole component in aqueous solutions at a pH of 10 or above will neutralize odors by oxidation, but only at a low rate. If the pH of the solution is lowered by acidification to a value of about 8 or less, sodium chlorite is converted to chlorine dioxide, a good oxidizer. At the lower pH values the oxidation potential of the sodium chlorite also increases. As the pH decreases further, the rate of formation of chlorine dioxide increases and a series of equilibrium mixtures between chlorine dioxide and the chlorite ion form. The overall oxidizing power of the composition increases because of the greater oxidation potential of the chlorine dioxide and because of the more reactive chlorite species.

Unfortunately, chlorine dioxide itself is offending to the olefactory senses even in trace amounts, i.e. about 5 ppm.

The art, therefore, has been faced with the problem that the reaction kinetics of aqueous compositions of alkali metal halogenites such as sodium chlorite are too slow. On the other hand, useful chlorine dioxide compositions require a low concentration of the chlorine dioxide if they are to avoid the aforementioned drawbacks.

Accordingly, it is an object of this invention to provide aqueous oxidizing compositions comprising an alkali metal halogenite with enhanced reactivity to eliminate odors rapidly but without appreciable formation of halogen oxide gases.

It is a further object of the invention to provide cleaning compositions.

It is a still further object of this invention to provide such compositions additionally containing a salt of a transition or post transition metal, or mixtures thereof.

SUMMARY OF THE INVENTION

The compositions of this invention are effective for deodorizing any of a variety of malodorous substrates including smoke and other household odors such as toilet and kitchen odors arising from a variety of sources including pets and food wastes or odors from cooking foods, especially burning odors. They are especially useful for deodorizing fabrics such as curtains and upholstery fabrics.

Compositions of the present invention comprise an alkali metal halogenite e.g. sodium chlorite in aqueous media together with an effective quantity of at least one salt of a transition or post transition metal, or mixtures of such salts. They also comprise such compositions additionally containing at least one selected ligand and, if desired, an alcohol to assist in stabilizing the sodium chlorite.

The composition may be used, for example, by spraying, or otherwise contacting, a fabric or other substrate from a container having a spray-pump mechanism, to effect deodorization. They also may be utilized as cleaning compositions.

The pH of the composition is largely dependent upon the constituents used. Typically, the pH will be about 4 to about 11. Preferably, so as to avoid or limit the formation of chloride dioxide, the pH should be slightly acidic or basic, most preferably above about 8.

The active components of the compositions of this invention function principally by reacting with the odor causing chemicals in the area to be treated to form reaction products that are odorless or at least non-offending. They thus reduce odors by chemical reaction, not by masking the odors with perfumes. However, perfumes may be included in the compositions to make them more pleasant to work with or, in some cases, to mask certain odors which are not neutralized by oxidation.

The alkali metal halogenite typically is present in an amount of at least 0.01%, sodium chlorite being the preferred oxidizing agent. Typically, the halogenite is present in an amount of 10% or less, although this is not intended to limit the upper concentration level.

The compositions will normally contain a sufficient level of the selected transition or post transition salt to effect an increase in the oxidation potential of the sodium chlorite. Wide variations are possible, depending on the salt selected. Of course, in some instances the salt chosen may also provide a second function, in which event the level for that function will govern. Typically, the metal ion will be present in the aqueous solution at a level of at least 0.0001% by weight. Amounts in excess of about 1% will not usually provide any additional benefit.

The perfumes, when employed in the compositions of the invention should be stable, i.e. not oxidized by the halogenite or, if unstable, should be employed together with a stabilizing amount of an anionic surfactant as described in copending and commonly owned patent application, serial number 54338 filed May 26, 1987.

A perfume, if employed, is normally utilized at a low concentration, i.e. 0.25% or less. If a perfume which is unstable in aqueous halogenite compositions is utilized, it will be in association with a stabilizing amount of an anionic surfactant, typically 10% or less of the selected surfactant.

In this disclosure and the appended claims, all amounts of the components of the compositions are defined in weight percent based on the total weight of the composition.

DETAILED DESCRIPTION OF THE INVENTION AND PREFERRED EMBODIMENTS

Attempts to prepare deodorant compositions containing alkali metal halogenites have been hampered for a number of reasons including those discussed above. In addition, the alkali metal halogenites, at least when compared to chlorine dioxide, are not considered to be strong oxidizers.

It has now been discovered that such compositions can be prepared in a useful form by including selected quantities of salts of transition and post transition metals or mixtures thereof. It appears that the transition or post transition metal ion may in some manner exhance the oxidation potential of the chlorite ion species, but this is not necessarily the mode of action of these salts.

Accordingly, the compositions of this invention are aqueous oxidizer compositions typically having a pH of from about 4 to 11, containing about 0.01% to about 15% preferably from about 0.05% to about 5% of an alkali metal halogenite together with at least 0.0001% of an ion of a transition or post transition metal or mixtures thereof. The compositions may optionally contain a perfume which may be a reactive perfume stabilized by an anionic surfactant.

In some instances the formation of chlorine dioxide is permitted, such compositions also containing the alkali metal halogenite and the transition metal or post transition metal salt ion. In such compositions the pH is in the lower region of the pH range, i.e. from about 4 to about 8. The presence of the chlorine dioxide does not appear to negatively influence the enhancement of oxidation potential enjoyed by the alkali metal halogenite and provided by the presence in solution of the salt ions.

It has been observed that the basic compositions of this invention can be improved utilizing certain ligands and secondary alcohols. The alcohols can be employed alone or together with the ligand. Both of these additives stabilize the compositions by inhibiting the decomposition of the chlorite, the formation of chlorine dioxide and the formation of precipitates.

The presently preferred secondary alcohols are isopropanol and secondary butyl alcohol. When employed, with or without a ligand the concentration of the alcohol is normally up to about 15% preferably 1% to 15% although appreciable variations are possible.

The term ligand as used in this disclosure and claims means a molecule, ion or atom that interacts with the transition or post transition metal salt and inhibits the formation of chlorine dioxide even at pH levels where chlorine dioxide would normally be produced. Typically ligands as employed herein are compounds which will form complexes with the central atom. Suitable ligands include oxalic, citric, acetic, polyacrylic and ethylenediamine tetraacetic acids, the alkali metal salts thereof and ammonia. Suitable concentrations of the ligand are about 10 times that of the metal salt. Therefore, the concentration range is from about 0.001% to 10%.

In the presently preferred practice of this invention for use as deodorizers, aqueous sodium chlorite compositions are employed which do not produce in excess of trace amounts of chlorine dioxide within one month of preparation, preferably three months, most preferably six months. By trace concentration is meant a level of chlorine dioxide detectable by ordinary analytical methods and/or by olefactory sensory evaluation, usually less than about 5 ppm, preferably less than 1 ppm, in said composition.

Sodium chlorite is preferably present in an amount of from about 0.01 to 15%, most preferably 0.05 to 1%. Compositions containing more than 10% are not appreciably more efficient than those containing less than this amount, but are within the scope of this invention.

Transition and post transition metals are a defined class of metals including metals that have filled or partially filled outer d orbitals, while post transition metals are those that have filled d orbitals and filled or partially filled p orbitals. Any of a variety of inorganic or organic salts of these metals may be usefully employed. Inorganic salts include, for example, halogen salts such as bromide or chloride salts, sulfate salts, phosphate salts and nitrate salts or salts with any other suitable anion. Organic salts include, for example, citrates, oxalates, acetates, and carboxylates such as stearate. Solubility of these salts is not a major factor so long as they ionize to some extent, to provide the requisite concentration of ions in solution. Of course, undissolved salt may be unattractive to the consumer, or may interfere with the dispensing mechanism of the product dispenser. The presently preferred salts are chloride salts such as cupric, zinc, stannic, or ferric chloride; sulfate salts such as cupric sulfate or citrate salts such as cupric citrate.

The transition and post transition metal salts are preferably present in the compositions in an amount suitable to provide a metal ion concentration of above about 0.0001%. Typically the metal ion concentration is from about 0.01 to about 1%, preferably from about 0.05 to about 0.1%. As with the chlorite concentration, there is no appreciable advantage in employing more than 1% of the selected salts. Therefore, it is preferred not to do so unless a particular salt also has a second functionality.

Certain transition or post transition metal salts will acidify the chlorite compositions of the present invention. For example, zinc chloride appears to ionize such that the zinc ion forms a coordination sphere with hydroxyl ions from the water constituent. Consequently, there is an excess of $H^+$ ions and a lowering of pH.

When the pH falls to less than about 8, chlorine dioxide begins to form, as previously noted. Because the conversion of chlorite to chlorine dioxide is pH dependent, the chlorine dioxide concentration may be regulated by regulating pH, for instance, with buffers as hereinafter explained.

Generally, the presence of chlorine dioxide is not preferred. When present in the compositions, however, it is at a level of less than about 5 ppm, preferably less than about 1 ppm.

Buffers are used to maintain pH within certain limits. In one aspect of the invention, the buffer may be selected to maintain pH above about 8. In such instances chlorine dioxide is not formed in detectable amounts. In another aspect, the pH level maintained by the buffer is such that a useful, but non-toxic concentration of chlorine dioxide is achieved.

Typically, the buffer or other pH adjustor will be present in an amount of less than about 10% by weight of the composition. Preferably, when utilized, the buffer will be from about 0.1 to about 5% of the composition, and will be in a sufficient quantity to maintain a basic pH. Suitable buffers include sodium carbonate, sodium borate, sodium bicarbonate and calcium hydroxide.

Alternatively, the solution may be initially prepared as a strongly alkaline solution with a strong alkali such as an alkali metal hydroxide, suitably sodium or potassium hydroxide.

If a perfume is employed in the practice of this invention, it should be stable or stabilizable in the presence of the alkali metal halogenite. Most perfumes which are useful in compositions of this nature contain oxidizable groups so that, as a practical matter, the selected perfume will be one which is stabilized by the use of an anionic surfactant as described in the aforementioned U.S. Ser. No. 54338 filed May 26, 1987 by Richard Hutchings, the disclosure of which is incorporated herein by reference.

Optionally, other adjuvants may be included in the compositions of the present invention, provided that such adjuvants do not exhibit incompatibility. For example, surfactants, colorants, chelating agents, sequestering agents, builders, and the like may be included. Care, however, must be exercized when selecting these optional materials to ensure compatibility. Thus, adjuvants with aldehyde or other easily oxidizable groups should be avoided since they will be oxidized by the halite present and undesirably decrease its concentration. Aldehydes will be oxidized to acids which will also increase the production of the halogen dioxide for the reasons explained above. This is normally undesirable. Stabilization of compositions containing colorant is disclosed in application U.S. Ser. No. 54347 filed May 26, 1987 by Richard Hutchings, et al, incorporated herein by reference thereto. The anion surfactants disclosed in U.S. Ser. No. 54347 and U.S. Ser. No. 54338 are especially preferred. The above mentioned adjuvants are incorporated in an amount suitable for attaining their particular function, typically in an amount of less than about 1%, except for surfactants which are generally less than about 10% preferably less than about 5%.

The compositions of this invention are useful for the elimination of a variety of odors such as pet odors and trash can odors. They are generally useful as room deodorants particularly for the elimination of smoke odors from soft surfaces including fabrics such as the fabrics in upholstery, carpets, curtains and drapes. Preferably, they are dispensed from a spray dispenser which provides a fine mist of the product. These compositions may also be used as general purpose cleaning/disinfectant agents for laundry and other household and janitorial cleaning purposes.

The following examples are given by way of illustration only and are not to be regarded as limitations of this invention many apparent variations of which are possible without departing from the spirit and scope thereof.

Except where noted, in the examples, the sodium chlorite was 80% active, the remainder being 5% sodium hydroxide and 15% sodium chloride.

EXAMPLE 1

The following compositions were made in accordance with the present invention. Each of these formulations contained 0.007 mols of the metal ion indicated, 0.5% sodium chlorite and water q.s. 100%.

| Metal | pH |
|---|---|
| Fe Cl$_3$.6H$_2$O | 4.0 |
| CrCl$_3$.6H$_2$O | 4.1 |
| Zn Cl$_2$ | 6.2 |
| Cu$_2$(C$_6$H$_4$O$_7$) | 9.5 |
| CuSO$_4$.5H$_2$O | 5.2 |

| Metal | pH |
|---|---|
| -continued | |
| CuCl$_2$.x H$_2$O | 4.5 |

EXAMPLE 2

This example illustrates the stabilization of the metal salt containing composition of the invention with the ligand sodium citrate.

| Control Formula | |
|---|---|
| Sodium Chlorite | 0.4% |
| Metal salt | 0.2% |
| Deionized water q.s | |

| Metal Salt | Control pH No ligand | pH with 2.3% Added Sodium Citrate |
|---|---|---|
| Sn Cl$_2$.2H$_2$O | 3 | 6 |
| Cr Cl$_3$.6H$_2$O | 4 | 6 |
| Cu Cl$_3$.XH$_2$O | 6 | 4 |
| Fe Cl$_3$.6H$_2$O | 4 | 7 |
| Zn Cl$_2$ | 6 | 8 |
| CuSO$_4$.5H$_2$O | 6 | 7 |

Chlorine dioxide was produce din all of the controls. None of the compositions containing citrate evidenced generation of chlorine dioxide even though the copper chloride, tin chloride and chromium chloride composition all were at an acid pH, and the other compositions were either neutral or slightly basic.

EXAMPLE 3

This example is similar to Example 2 except that ethylenediamine tetraacetate (EDTA) was used as a ligand. No precipitates were formed in any of the EDTA containing solutions and no chlorine dioxide was produced.

| Control Formula | |
|---|---|
| Sodium Chlorite | 0.4% |
| Metal salt | 0.2% |
| Deionized water q.s | |

| Metal Salt | Control pH No ligand | pH with 2.3% Added EDTA |
|---|---|---|
| Sn Cl$_2$.2H$_2$O | 3 | 9 |
| Cr Cl$_3$.6H$_2$O | 4 | 9 |
| Fe Cl$_3$.6H$_2$O | 4 | 11 |
| Zn Cl$_2$ | 6 | 11 |
| Cu Cl$_3$.XH$_2$O | 6 | 11 |

EXAMPLE 4

This example is similar to Examples 2 and 3 and shows the use of sodium oxalate as a ligand stabilizer. No precipitates or chlorine dioxide formed in any of the oxalate containing compositions.

| Control Formula | |
|---|---|
| Sodium Chlorite | 0.4% |
| Metal salt | 0.2% |
| Deionized water q.s | |

| Metal Salt | Control pH No ligand | pH with 0.2% Added Sodium Oxalate |
|---|---|---|
| Sn Cl$_2$.2H$_2$O | 3 | 6 |

-continued

|  |  |  |
|---|---|---|
| Fe Cl$_3$.6H$_2$O | 4 | 8 |
| Cu So$_4$.5H$_2$O | 5 | 10 |
| Zn Cl$_2$ | 6 | 9 |
| Cu Cl$_3$.XH$_2$O | 5 | 10 |

EXAMPLE 5

The following compositions were prepared to illustrate compositions of the invention containing a metal salt, a ligand and a perfume.

| A | B |
|---|---|
| 82.07% deionized water | 82.03% deionized water |
| 0.5% sodium chlorite | 0.5% sodium chlorite |
| 2.32% sodium citrate | 2.32% sodium citrate |
| 0.1% zinc chloride | 0.1% zinc chloride |
| 15% isopropyl alcohol | 15% isopropyl alcohol |
| 0.01% perfume | 0.05% perfume |

EXAMPLE 6

This example shows the efficacy of certain ligands to stabilize the basic compositions of this invention both with respect to pH and retention of sodium chlorite in the composition

| Base Formula | Percent Ligand |
|---|---|
| Sodium Chlorite 0.4% | Citric Acid 0.75% |
| Isopropyl Alcohol 5% | Sodium Citrate 2.32% |
| Zinc Chloride 0.1% | Sodium Acetate 0.33% |
| Ligand | EDTA 1.54% |
| Deionized Water Q.S | Sodium Polyacrylate 0.02% (PAA) |

| Ligand | Initial PH | Final PH 28 DAYS/ 125° F. | Final PH 100° F./90 DAYS | Final PH Room Temp 90 DAYS |
|---|---|---|---|---|
| Citric Acid | 7.2 | 7.2 | 9.1 | 9.2 |
| Citrate | 7.6 | 7.8 | 8.1 | 8.1 |
| Acetate | 6.8 | 6.2 | 6.4 | 6.5 |
| EDTA | 11.1 | 9.7 | 9.8 | 9.3 |
| PAA | 6.5 | 6.0 | 6.6 | 6.5 |

| Ligand | PPM Chlorite Initial | PPM Chlorite 28 DAYS 125° F. | PPM Chlorite 100° F/90 DAYS | PPM Chlorite Room Temp |
|---|---|---|---|---|
| Citric Acid | 3300 | 65 | 460 | 3000 |
| Citrate | 3200 | 3100 | 3100 | 3200 |
| Acetate | 3400 | 2600 | 3000 | 3600 |
| EDTA | 3300 | 2800 | 3200 | 3000 |
| PAA | 3300 | 2300 | 2800 | 3200 |

1. No chlorine dioxide was formed
2. All room temperature samples stable to chlorite loss
3. The acetate and PAA sample maintained acidic pH's

EXAMPLE 7

Cloths 1 to 11 below were treated with the recited compositions and rated for efficacy of smoke odor removal.

1. 0.25% sodium chlorite, 0.05% copper citrate
2. 0.1% sodium chlorite, 0.01% copper citrate
3. 0.5% sodium chlorite, 0.1% chromium chloride, 0.1% sodium hydroxide
4. 0.5% sodium chlorite, 0.1% tin chloride, 0.1% sodium hydroxide
5. 0.5% sodium chlorite, 0.1% cobalt chloride
6. No smoke odor applied
7. Unidentified smoked cloth
8. Water
9. 2.0% sodium chlorite, 1.0% copper citrate
10. 0.5% sodium chlorite, 0.1% copper citrate
11. 0.5% sodium chlorite The efficacy of these compositions was evaluated as follows. Test cheese cloths were saturated with smoke odor in a test chamber for about one hour. Equal amounts of the above compositions were applied by spraying to the test cloths. Cloths 6 and 7 were used as controls. The smoke treated cloths were rated for smoke odor blindly by a panel of judges, the cloth's acting as a basis of comparison. A suitable number of observations were made so that the results were statistically significant to a 95% confidence level. The values above are reported on a scale normalized to 0 to 10 (zero meaning total perceived smoke odor elimination). The results are shown below.

| Cloth | Odor Rating 30 minutes | Odor Rating 3 hours | Retained Smoke Odor 3 hours |
|---|---|---|---|
| 1 | 8.2 | 1.9 | yes |
| 2 | 7.9 | 3.3 | No |
| 3 | 3.9 | 0.9 | No |
| 4 | 3.7 | 0.9 | No |
| 5 | 9.0 | 3.1 | No |
| 6 | 2.4 | 0 | No |
| 7 | 4.7 | 5.3 | Yes |
| 8 | 9.8 | 0.7 | Yes |
| 9 | 2.9 | 1.1 | No |
| 10 | 2.4 | 0.7 | No |
| 11 | 7.2 | 2.2 | Yes |

EXAMPLE 8

The following compositions were evaluated for reduction of smoke odor using the same procedure as in Example 7 except that the samples were allowed to air dry for 5 hours after treatment.

| Composition | Odor Rating |
|---|---|
| 5% sodium chlorite plus 1% copper citrate | 0.64 |
| 5% sodium chlorite plus 0.1% copper citrate | 0.86 |
| 0.5% sodium chlorite plus 0.1% zinc chloride | 1.57 |

EXAMPLE 9

This example illustrates the ability of certain alcohols to stabilize the sodium chlorite in the basic compositions of this invention.

| Control Formula |
|---|
| 0.4% sodium chlorite (100% active basis) |
| 0.1% zinc chloride |
| 99.5% deionized water |

| Test Formulas |
|---|
| 5% alcohols (Samples B-K) |
| 0.4% sodium chlorite (100% active basis) |
| 0.1% zinc chloride |
| 94.5% deionized water |
| 14 Day Time Period |

| Formula #/Alcohol | System pH | Chlorine Dioxide Present |
|---|---|---|
| A. Control | 6.4 | Yes |
| B. Isopropyl | 6.4 | No |
| C. Ethanol | 6.5 | Yes |
| D. Methanol | 6.4 | Yes |
| E. N-Propanol | 6.5 | Yes |
| F. N-Butanol | 6.6 | Yes |

| -continued | | |
|---|---|---|
| G. Isobutanol | 6.6 | Yes |
| H. 2-Butanol | 6.2 | No |
| I. Tert-butanol | 6.5 | Yes |
| J. Ethylene glycol | 6.9 | Yes |
| K. Propylene glycol | 6.7 | Yes |

Note that no ligands are present in these formulations. As will be seen from the above only secondary alcohols stabilized the compositions as evidenced by the fact that chlorine dioxide was released in all other compositions as would normally be expected since all compositions were acidic.

This example was repeated with similar compositions utilized ethanol, isopropyl alcohol and secondary butyl alcohol and tap water instead of deionized water since it was postulated that the dissolved chlorine in the tap water was responsible for the destabilization of the sodium chlorite. Again it was observed that the secondary alcohols were useful as stabilizing agents.

What is claimed:

1. An aqueous oxidizer composition having a pH of from about 4 to 11 comprising on a weight basis from about 0.01 to about 10% of an alkali metal halogenite and a salt selected from the group consisting of salts of transition and post transition metals and mixtures thereof, said salt being present in a concentration sufficient to obtain a metal ion concentration of at least about 0.0001%, at least about 0.001% of a ligand that interacts with the transition or post transition metal salt and inhibits the formation of chlorine dioxide and from about 1% to about 15% of a secondary alcohol.

2. The composition of claim 1 wherein the alkali metal halogenite is sodium chlorite.

3. The composition of claim 2 wherein the salt cation is selected from the group consisting of zinc, stannic, ferric, cupric salts and wherein the salt anion is selected from the group consisting of chloride, sulfate, citrate and phosphate.

4. The composition of claim 2 wherein the sodium chlorite present in an amount of from about 0.05 to about 1%.

5. The composition of claim 2 or 4 wherein the pH is above 8.

6. The composition of claim 5 including a buffer effective to maintain the pH above 8.

7. The composition of claim 6 wherein the buffer is selected from the group consisting of sodium carbonate, sodium borate, sodium bicarbonate and calcium hydroxide.

8. The composition of claim 5 wherein the salt is selected from the group consisting of zinc chloride, stannic chloride, ferric chloride, cupric chloride, cupric sulfate and cupric citrate.

9. The composition of claim 5 wherein the salt is cupric citrate.

10. The composition of claim 1 wherein the alcohol is isopropanol or secondary butyl alcohol.

11. A method of deodorizing malodorous substrates which comprise contacting the substrate with an amount of a composition of claim 1, 2, 3, 5 or 8 which is sufficient to effect deodorization.

12. A method of cleaning/disinfecting a substrate which comprises the substrate with a cleaning/disinfecting amount of a composition of claim 1, 2, 3, 5 of 8.

13. A composition of claim 1 wherein the ligands are selected from the group consisting of oxalic, citric, acetic, polyacrylic and ethylenediamine, tetracetic acids and alkali metal slats thereof and ammonia.

* * * * *